United States Patent [19]

Lamos et al.

[11] Patent Number: 5,037,738

[45] Date of Patent: Aug. 6, 1991

[54] SIMULTANEOUS ASSAY FOR GLUCOSE AND UREA

[75] Inventors: Michael L. Lamos, Irving, Tex.; David A. Yost, Round Lake Park, Ill.; Diane M. Bates, Roanoke, Tex.

[73] Assignee: Abbott Laboratories, Abbott Park, Ill.

[21] Appl. No.: 135,209

[22] Filed: Dec. 21, 1987

Related U.S. Application Data

[63] Continuation-in-part of Ser. No. 57,842, Jun. 3, 1987, abandoned.

[51] Int. Cl.$^5$ .......................... C12Q 1/58; C12Q 1/54; C12Q 1/36; C12Q 1/32
[52] U.S. Cl. .......................................... 435/12; 435/14; 435/25; 435/26; 435/18; 435/4; 435/15; 436/95; 436/108
[58] Field of Search .................... 435/15, 4, 12, 14, 25, 435/26, 18; 436/95, 108

[56] References Cited

U.S. PATENT DOCUMENTS 3,964,870 6/1976 Tiedemann et al. .................. 23/253
4,425,427 1/1984 Luderer ................................ 435/10

FOREIGN PATENT DOCUMENTS 0094161 11/1983 European Pat. Off. .
0140899 11/1981 Japan .

OTHER PUBLICATIONS

Fu, P. C. et al., *Adv. Autom. Anal.*, Technicon Int. Congr. (1973), vol. 1, pp. 171-178.
Fu, P. C. et al., Chemical Abstracts, vol. 82, No. 21, Abstract No. 135224 q (1975).
Kerscher, L. et al., "Urea", in *Methods of Enzymatic Analysis*, vol. VIII, 3 ed., (Bergmeyer, ed.) Weinheim, FRG, pp. 444-448 (1984).
Möllering, H. et al., "Visualization of NAD(-P)-Dependent Reactions" in *Methods of Enzymatic Analysis*, vol. I, 2 ed., (Bergmeyer, ed.), FRG, pp. 136-144 (1974).
Vormbrock, R "UV-Method with Glucose Dehydrogenase", in Methods of Enzymatic Analysis, vol. VI, (Bergmeyer, ed.), 3 ed., FRG, pp. 172-178 (1984).

*Primary Examiner*—Esther L. Kepplinger
*Assistant Examiner*—Toni R. Scheiner
*Attorney, Agent, or Firm*—Daniel W. Collins

[57] ABSTRACT

A method for the simultaneous determination of glucose and urea in a specimen with a single reagent system. A reagent system containing a reactant for each of glucose and urea to be determined is added to a specimen. The reagent system is reacted with the specimen such that each of glucose and urea react with their respective reactant simultaneously. Each reactant is selected such that it is capable of giving an absorbance band for glucose and urea which permits their simultaneous determination. The change in absorbance or fluorescence of the resulting reaction mixture is monitored at a plurality of wavelengths which are characteristic for each of glucose and urea.

34 Claims, No Drawings

SIMULTANEOUS ASSAY FOR GLUCOSE AND UREA

CROSS REFERENCE TO RELATED APPLICATIONS

This application is a continuation in part of U.S. Ser. No. 057,842, filed June 3, 1987 now abandoned.

BACKGROUND OF THE INVENTION

The present invention relates to a simultaneous assay for glucose and urea with a single reagent by monitoring concurrent reactions which produce changes in the electromagnetic radiation absorbance characteristics of the sample. In one aspect, the invention relates to the simultaneous measurement of glucose and urea in blood serum by monitoring two concurrent reactions at two or more different wavelengths.

In the field of diagnostics, various assays are designed to identify or quantify an analyte, such as glucose or urea, which may be present in a sample material. Unfortunately the assay is usually only specific to one analyte even though it may be desirable to diagnose more than one analyte for any given sample. This leads to multiple testing on the same sample which increases diagnosis cost and decreases efficiency. It is therefore desirable to develop diagnostic testing which can identify or quantify multiple analytes in an efficient manner.

For example, glucose and urea are two of the more common tests performed in the clinical chemistry laboratory. Analysis of glucose is typically done using either a hexokinase or glucose oxidase method (Tietz, N. W., *Textbook of Clinical Chemistry*, 1986, p. 785). In the hexokinase method glucose is converted to glucose-6-phosphate hexokinase and adenosine triphosphate. Glucose-6-phosphate then reacts with glucose-6-phosphate dehydrogenase (G-6-PDH) to produce 6-phosphogluconate, with the concomitant reduction of nicotinamide-adenine dinucleotide (NAD) producing an increase in absorbance at 340 nm. The glucose oxidase method involves oxidation of glucose to gluconic acid and hydrogen peroxide by glucose oxidase. The hydrogen peroxide then reacts with peroxidase and a chromogenic oxygen acceptor to produce a color change in the 400–550 nm range. A third method for identifying glucose uses glucose dehydrogenase (Tietz, N. W., *Textbook of Clinical Chemistry*, 1986, p. 790). Glucose dehydrogenase converts glucose to gluconolactone with the concomitant reduction of NAD.

Analysis of urea is typically done using the urease/-glutamate dehydrogenase method (Tietz, N. W., *Textbook of Clinical Chemistry*, 1986, p. 1268). Urease converts urea to ammonia and carbon dioxide. The ammonia produced reacts with glutamate dehydrogenase and alpha ketoglutarate to produce glutamate, with the concomitant oxidation of NADH producing a decrease in absorbance at 340 nm.

The assays mentioned above are performed with separate reagents in separate cuvettes. This costs the clinical chemistry lab time and money. By combining the two tests into one test the lab would be able to realize an increase in productivity and also a cost savings.

Combining the two tests is not a straightforward task. Reagents must be selected that allow precise measurement of one analyte (i.e., glucose), without interfering in the measurement of the second analyte (i.e., urea). For example, the combination of the glucose hexokinase and urea urease methods is eliminated by the fact that both use the NAD/NADH reaction. The combination of the glucose oxidase and urea urease methods is eliminated by the fact that peroxidase in the glucose reaction would oxidize the NADH in the urea reaction.

One way of combining the two assays in a single reaction vessel is to do a sequential assay such as disclosed in U.S. Pat. No. 4,425,427 to Luderer. European Application No. 133064 to Cam discloses another sequential assay where reagent for a first component is added to the vessel and at some later time a concentration is determined for the first component. Then a second reagent, which either quenches the first reaction or is added after the first reaction is complete, is added to the vessel to trigger a reaction with the second component. At some later time the concentration of the second component is determined. These reactions can either be monitored at the same wavelength or at different wavelengths (either through the use of filter wheels or diode arrays).

U.S. Pat. No. 3,925,162 describes the simultaneous measurement of enzyme activity in body fluids. In this approach the substrate for each of the enzymes to be identified are added to a reaction medium with other reagents and changes in the absorbance or fluorescence of the resulting reaction system are measured. The present invention is an approach where a single reagent system is used to simultaneously identify or quantify at least two analytes by monitoring the electromagnetic signal of the reaction mixture.

SUMMARY OF THE INVENTION

The present invention is directed toward a method for the simultaneous determination of glucose and urea with a single reagent system. The method comprises adding a reagent system containing a reactant for each of the analytes to be determined, each reactant being selected such that it is capable of giving a unique electromagnetic radiation absorbance for the particular analyte which does not interfere with the determination of the other analyte. The analytes are reacted with their respective reactant under conditions such that the reaction takes place simultaneously. The concentration of the analyte is determined by measuring changes in absorbance or fluorescence of the resulting reaction mixture at a plurality of wavelengths which are characteristic for each of the analytes to be determined. The analyte concentration is measured by either monitoring the reaction rates or the reaction endpoint.

In another aspect the present invention is a method for the simultaneous determination of glucose and urea with a single reagent system by adding a reagent system containing a chromophore for each of the analytes to be determined, each chromophore being selected such that it is capable of giving a unique absorbance band for the particular analyte which does not interfere with the determination of the other analyte. The analytes are reacted with their respective chromophore under conditions such that the reaction takes place simultaneously. The concentration of the analytes is determined by monitoring changes in absorbance or fluorescence of the resulting reaction mixture at a plurality of wavelengths which are characteristic for each of the analytes to be determined.

In a preferred embodiment the reagent system is an enzyme system where chromophores are chosen for glucose and urea which have distinguishable energy spectra such that they can be simultaneously determined. Preferred chromophores for the determination of glucose are NAD(H), NADP(H), thio-NAD(H), thio-NADP(H), hypoxanthine-NAP(H), hypoxanthine-NADP(H), pyrroloquinone, peroxide/chromogenic oxygen acceptor or analogs thereof. Preferred chromophores for the determination of urea are NAD(H), NADP(H), thio-NAD(H), thio-NADP(H), hypoxanthine-NAD(H), hypoxanthine-NADP(H), indicator dyes or analogs thereof. The NAD or NAP chromophores can be used in either a reduced or oxidised state as is indicated by the (H). This is because either form can be used to monitor a change in absorbance or fluorescence.

A reagent system useful in performing the present simultaneous assay comprises hexokinase, ATP, NADP specific glucose-6-phosphate dehydrogenase (G-6-PDH), magnesium and thio-NADP for the determination of glucose; and urease, pyruvate, lactate dehydrogenase (LDH) inhibitor, NADH specific alanine dehydrogenase (ADH), and NADH for the determination of urea. Preferably, the LDH inhibitor is oxalate.

The simultaneous assay can also be performed using a reagent comprising hexokinase, ATP, NADP specific G-6-PDH, magnesium and thio NADP for the determination of glucose; and urease, alpha ketoglutarate, NADH specific GLDH, and NADH for the determination of urea.

Another reagent system for performing the simultaneous assay can comprise NADP specific glucose dehydrogenase (with or without mutarotase) and thio-NADP for the determination of glucose; and urease, 2-oxoisocaproate, NADH specific leucine dehydrogenase, an LDH inhibitor and NADH for the determination of urea.

The simultaneous assay can also be performed with a reagent system comprising glucose dehydrogenase (with or without mutarotase) and thio NADP for the determination of glucose; and urease, alpha ketoglutarate, GLDH, and NADH for the determination of urea The glucose dehydrogenase reaction can also be coupled to the following urea reaction. Urease is used to produce ammonia from urea. The ammonia is reacted with L-glutamate and ATP in the presence of glutamine synthetase to produce ADP. The ADP is reacted with phosphoenolpyruvate in the presence of pyruvate kinase to produce pyruvate. The pyruvate is reacted with NADH in the presence of LDH to produce lactate and oxidized NAD.

Both the hexokinase/G-6-PDH and glucose dehydrogenase assays can be coupled to a urea reaction comprising urease, 2-oxoisocapnoate, oxalate, leucine dehydrogenase, and NADH for the determination of urea.

In yet another reagent system for performing the simultaneous assay can comprise glucose dehydrogenase and NAD in concentrations sufficient to allow a rate determination of glucose and urease and an indicator dye in concentrations sufficient to allow an endpoint determination of urea.

DETAILED DESCRIPTION OF THE INVENTION

The present invention relates to a method for simultaneously measuring a plurality of analytes in a biological fluid. The method utilizes a single reagent for measurement of each of the analytes by monitoring several electromagnetic signals simultaneously.

The electromagnetic signals can be monitored simultaneously by a spectrophotometer, or spectrofluorometer. The measurement of changes in the reaction mixture can be carried out on any of the instruments by conventional procedures. The particular change in the system, i.e., wavelength, is not critical, but it is preferable that the changes or differences in wavelength be as great as possible provided they can be monitored simultaneously. Preferably, the reaction mixture spectra is simultaneously monitored to observe reaction rate changes as well as endpoint determinations.

In a simultaneous assay a reagent containing all the components for reaction with the analytes to be measured are added to the sample and the reactions are monitored by the instrument. Typically, a simultaneous assay is done in a single cuvette with a single reagent, eliminating the need for a second reagent dispense or other optional steps generally associated with multiple analyte assays.

A key to the design of a simultaneous assay is the selection of reagents that will allow the reactions to proceed simultaneously, but without interfering with each other in determination of results in the clinically relevant range. A reactant is chosen for each of the analytes to be determined, each reactant being selected such that it is capable of giving a unique electromagnetic radiation absorbance for the particular analyte which permits determination of other analytes. A reactant can be a chromophore or indicator dye where the reaction will be monitored by spectra wavelength. For example, by choosing appropriate chromophores an assay can be developed that will measure glucose and urea simultaneously as described below.

Preferred chromophores for the determination of glucose are NAD(H), NADP(H), thio-NAD(H), thio-NADP(H), hypoxanthine-NAP(H), hypoxanthine-NADP(H), pyrroloquinone, peroxide/chromogenic oxygen acceptor or analogs thereof. Preferred chromophores for the determination of urea are NAD(H), NADP(H), thio-NAD(H), thio-NADP(H), hypoxanthine-NAD(H), hypoxanthine-NADP(H), indicator dyes or analogs thereof. The NAD or NAP chromophores can be used in either a reduced or oxidised state as is indicated by the (H). This is because either form can be used to monitor a change in absorbance or fluorescence.

The reagent and sample are mixed such that each of the analytes is contacted with their respective reactant under conditions such that the reaction takes place simultaneously. The addition and mixing of the sample and reagent is monitored by instrumentation appropriate for the reaction taking place such as measuring changes in absorbance or fluorescence of the resulting reaction mixture at a plurality of wavelengths which are characteristic for each of the analytes to be determined.

Preferably the monitoring of the reaction mixture is begun as soon as the reagent and sample are intermixed. This allows for monitoring of changes in either the reaction rate or endpoint reaction for the particular electromagnetic signal being monitored.

In one example the subject method allows for the simultaneous measurement of glucose and urea in blood serum using a single reagent. The glucose and urea reactions proceed at the same time, with measurement of the two different reactions monitored at two separate wavelengths by a spectrophotometer. The spectrophotometer employs a diode array detector having the capability of simultaneously monitoring many wavelengths.

In one aspect, the measurement of glucose is through the use of nicotinamide-adenine dinucleotide phosphate (NADP) specific glucose-6-phosphate dehydrogenase (G-6-PDH) coupled with thio-NADP. The absorbance maximum of thio-NADP is at 404 nm, with relatively little absorbance change at 340 nm. This allows coupling of the glucose reagent with a urea reagent using reduced nicotinamide-adenine dinucleotide (NADH) and alanine dehydrogenase (ADH) since the NADH can be monitored at 340 nm with little or no absorbance change at 404 nm.

In another approach the G-6-PDH/thio-NADP reaction can be coupled with a urea reagent using urease, alpha-ketoglutarate, NADH, and glutamate dehydrogenase. In yet another approach, the G-6-PDH/thio-NADP reaction is coupled with a urea reagent using urease, NADH, leucine dehydrogenase, and 2-oxoisocaproate or analogs thereof. It should be noted that in the preceding approaches the GDH/thio-NADP reaction may replace the G-6-PDH/thio-NADP reaction.

In another aspect the GDH/thio-NADP reaction can be coupled with a urea reagent using urease, L-glutamate, ATP, glutamine synthetase, phosphoenolpyruvate, pyruvate kinase, NADH, and LDH.

Alternatively, the G-6-PDH/thio-NADP or GDH/thio-NADP reaction can be coupled with an indicator reaction similar to that described by Chang in U.S. Pat. No. 3,950,226. Here non-specific glucose dehydrogenase (E.C.1.1.1.47) is used and the glucose reaction is monitored by following the change in absorbance at 340 nm as NAD is reduced to NADH. Tie urea reaction is monitored by following the change in absorbance of an indicator dye as ammonia is produced by the action of urease on urea. Since the urea reaction is dependent on a change in pH, sensitivity can be increased by using a weakly buffered system and by adjusting the pH away from the pK of the buffer.

Another approach is to use glucose dehydrogenase (E.C.1.1.99.10) specific for pyrroloquinone dyes such as 2,6-dichlorophenol indophenol (DCIP). The glucose reaction is monitored at 600 nm as DCIP is reduced. The urea part of the assay uses the ADH/NADH (alternatively, GLDH/NADH, leucine dehydrogenase/-NADH or glutamine synthetase/NADH) method and the urea reaction is monitored at 340 nm as NADH is oxidized to NAD.

In a preferred approach the glucose part of the assay consists of hexokinase, ATP, magnesium, G-6-PDH, and thio-NADP. Glucose in the sample is phosphorylated by hexokinase in the presence of ATP. The glucose-6-phosphate produced is subsequently oxidized by an NDP specific G-6-PDH with the concomitant reduction of thio-NADP to thio-NADPH. The reduction of thio-NADP is monitored at 404 nm.

The urea art of the assay consists of urease, pyruvate, an LDH inhibitor such as oxalate, ADH, and NADH. Urea in the sample is hydrolyzed to carbon dioxide and ammonia by urease. Ammonia subsequently reacts with ADH in the presence of pyruvate with the concomitant oxidation of NADH to NAD. The oxidation of NADH is monitored at 340 nm. The preferred LDH inhibitors are oxalate and oxamate which inhibit LDH in the sample.

ADH preferentially uses NADH over thio-NADPH and so production of thio-NADPH in the glucose part of the assay will not interfere with the determination of urea. Also, since the G-6-PDH is specific for NADP, production of NAD in the urea part of the assay will not interfere with the determination of glucose.

Thio-NADPH has a maximum absorbance at 404 nm, but also has an absorbance at 340 nm which does not change in going from oxidized to reduced form. Thus the combined absorbance at 340 nm of thio-NADP and NADH limits the amount of either which can be in solution. The optimum concentrations will be in the range of 0.1 to 0.8 mM. Varying the ratio of NADH to thio-NADP in the reagent will affect the linear ranges of the chromophores.

To increase linearity for urea, an option is to increase the NADH concentration and read the delta absorbance at 364 nm. However, since there is an absorbance change from thio-NADP at 364 nm, a correction factor will need to be applied to the 364 nm wavelength reading.

A number of ADH substrates were successfully tried, with pyruvate proving optimal. Likewise, a number of LDH inhibitors were successfully tried, with oxalate proving optimal.

A number of buffer systems were tried at various pH values. Triethanolamine (TEA) buffer (pH 8.0–8.8) performed optimally.

To further describe the instant invention the following examples are provided.

EXAMPLE 1

Glucose/Urea Simultaneous Assay

The following procedure describes a method for performing a simultaneous assay for glucose and urea by monitoring the endpoints of both the glucose and the urea reactions. A reagent system was prepared by mixing the following (U/L is units per liter and mM is millimoles per liter):

1000 U/L hexokinase
2000 U/L G-6-PDH
2.0 mM ATP
1.0 mM magnesium aspartate
0.25 mM thio-NADP
100000 U/L urease
40000 U/L ADH
10 mM pyruvate
40 mM oxalate
0.6 mM NADH
50 mM TEA pH 8.0

Sample is added to the reagent at a ratio of 1:201 and the reaction is allowed to proceed. After 3 minutes the absorbance is read at 340 nm and at 404 nm. Concentrations are calculated by comparison with standard curves.

EXAMPLE 2

Glucose/Urea Simultaneous Assay

The following procedure describes a method for performing a simultaneous assay for glucose and urea by monitoring the glucose rate of reaction and the urea reaction endpoint. A reagent system was prepared by mixing the following (U/L is units per liter and mM is millimoles per liter):

1000 U/L hexokinase
200 U/L G-6-PDH
2.0 mM ATP
1.0 mM magnesium aspartate
0.25 mM thio-NADP 100000 U/L urease
40000 U/L ADH
10 mM pyruvate
40 mM oxalate
0.6 mM NADH
50 mM TEA pH 8.0

Sample is added to the reagent at a ratio of 1:201 and the reaction is allowed to proceed. The glucose rate of reaction is monitored at 404 nm by taking a read every 60 sec for three minutes, starting at 60 seconds. After 3 minute the absorbance is read at 340 nm. Concentrations are calculated by comparison with standard curves.

EXAMPLE 3

Glucose/Urea Simultaneous Assay

The following procedure describes a method for performing a simultaneous assay for glucose and urea by monitoring the glucose reaction endpoint and the urea reaction rate. A reagent system was prepared by mixing the following (U/L is units per liter and mM is millimoles per liter):

1000 U/L hexokinase
2000 U/L G-6-PDH
2.0 mM ATP
1.0 mM magnesium aspartate
0.25 mM thio-NADP
100000 U/L urease
3000 U/L ADH
10 mM pyruvate
40 mM oxalate
0.25 mM NADH
50 mM TEA pH 8.0

Sample is added to the reagent at a ratio of 1:201 and the reaction is allowed to proceed. The urea is followed at 340 nm by reading every 60 seconds for three minutes. After 3 minutes the absorbance is read at 404 nm. Concentrations are calculated by comparison with standard curves.

EXAMPLE 4

Glucose/Urea Simultaneous Assay

The following procedure describes a method for performing a simultaneous assay for glucose and urea by monitoring the rates of both the glucose and the urea reactions. A reagent system was prepared by mixing the following (U/L is units per liter and mM is millimoles per liter):

1000 U/L hexokinase
200 U/L G-6-PDH
2.0 mM ATP
1.0 mM magnesium aspartate
0.25 mM thio-NADP
100000 U/L urease
3000 U/L ADH
10 mM pyruvate
40 mM oxalate
0.25 mM NADH
50 mM TEA pH 8.0

Sample is added to the reagent at a ratio of 1:201 and the reaction is allowed to proceed. Every 60 seconds for three minute the absorbance is read at 340 nm and at 404 nm. Concentrations are calculated by comparison with standard curves.

EXAMPLE 5

Glucose/Urea Simultaneous Assay

The following procedure describes a method for performing a simultaneous assay for glucose and urea by monitoring the endpoints of both the glucose and the urea reactions. A reagent system was prepared by mixing the following (U/L is units per liter and mM is millimoles per liter):

10,000 U/L glucose dehydrogenase
2000 U/L mutarotasg
0.25 mM thio-NADP
100000 U/L urease
40000 U/L ADH
10 mM pyruvate
40 mM oxalate
0.6 mM NADH
50 mM TEA pH 8.0

Sample is added to the reagent at a ratio of 1:201 and the reaction is allowed to proceed. After 3 minutes the absorbance is read at 340 nm and 404 nm. Concentrations are calculated by comparison with standard curves.

EXAMPLE 6

Glucose/Urea Simultaneous Assay

The following procedure describes a method for performing a simultaneous assay for glucose and urea by monitoring the glucose rate of reaction and the urea reaction endpoint. A reagent system was prepared by mixing the following (U/L is units per liter and mM is millimoles per liter):

1000 U/L glucose dehydrogenase
200 U/L mutarotase
0.25 mM thio-NADP
100000 U/L urease
40000 U/L ADH
10 mM pyruvate
40 mM oxalate
0.6 mM NADH
50 mM TEA pH 8.0

Sample is added to the reagent at a ratio of 1:201 and the reaction is allowed to proceed. The glucose rate of reaction is monitored at 404 nm by taking a read every 60 seconds for three minutes, starting at 60 seconds. After 3 minutes the absorbance is read at 340 nm. Concentrations are calculated by comparison with standard curves.

EXAMPLE 7

Glucose/Urea Simultaneous Assay

The following procedure describes a method for performing a simultaneous assay for glucose and urea by monitoring the glucose reaction endpoint and the urea reaction rate. A reagent system was prepared by mixing the following (U/L is units per liter and mM is millimoles per liter):

10,000 U/L glucose dehydrogenase
2000 U/L mutarotase
0.25 mM thio-NADP
100000 U/L urease
3000 U/L ADH
10 mM pyruvate
40 mM oxalate
0.6 mM NADH
50 mM TEA pH 8.0

Sample is added to the reagent at a ratio of 1:201 and the reaction is allowed to proceed. The urea is followed at 340 nm by reading every 60 seconds for three minutes. After 3 minutes the absorbance is read at 404 nm. Concentrations are calculated by comparison with standard curves.

EXAMPLE 8

Glucose/Urea Simultaneous Assay

The following procedure describes a method for performing a simultaneous assay for glucose and urea by monitoring the rates of both the glucose and the urea reactions. A reagent system was prepared by mixing the following (U/L is units per liter and mM is millimoles per liter):

1000 U/L glucose dehydrogenase
200 U/L mutarotase
0.25 mM thio-NADP
100000 U/L urease
3000 U/L ADH
10 mM pyruvate
40 mM oxalate
0.6 mM NADH
50 mM TEA pH 8.0

Sample is added to the reagent at a ratio of 1:201 and the reaction is allowed to proceed. Every 60 seconds for three minutes the absorbance is read at 340 nm and at 404 nm. Concentrations are calculated by comparison with standard curves.

EXAMPLE 9

Glucose/Urea Simultaneous Assay

The following procedure describes a method for performing a simultaneous assay for glucose and urea by monitoring the endpoints of both the glucose and the urea reactions. A reagent system was prepared by mixing the following (U/L is units per liter and mM is millimoles per liter):

1000 U/L hexokinase
2000 U/L G-6-PDH
2.0 mM ATP
1.0 mM magnesium aspartate
0.25 mM thio-NADP
100000 U/L urease
8000 U/L GLDH
10 mM alpha ketoglutarate
0.6 mM NADH
50 mM TEA pH 8.0

Sample is added to the reagent at a ratio of 1:201 and the reaction is allowed to proceed. After 3 minutes the absorbance is read at 340 nm and at 404 nm. Concentrations are calculated by comparison with standard curves.

EXAMPLE 10

Glucose/Urea Simultaneous Assay

The following procedure describes a method for performing a simultaneous assay for glucose and urea by monitoring the glucose rate of reaction and the urea reaction endpoint. A reagent system was prepared by mixing the following (U/L is units per liter and mM is millimoles per liter):

1000 U/L hexokinase
200 U/L G-6-PDH
2.0 mM ATP
1.0 mM magnesium apartate
100000 U/L urease
8000 U/L GLDH
10 mM alpha ketoglutarate
0.6 mM NADH
50 mM TEA pH 8.0

Sample is added to the reagent at a ratio of 1:201 and the reaction is allowed to proceed. The glucose rate of reaction is monitored at 404 nm by taking a read every 60 seconds for three minutes, starting at 60 seconds. After 3 minutes the absorbance is read at 340 nm. Concentrations are calculated by comparison with standard curves.

EXAMPLE 11

Glucose/Urea Simultaneous Assay

The following procedure describes a method for performing a simultaneous assay for glucose and urea by monitoring the glucose reaction endpoint and the urea reaction rate. A reagent system was prepared by mixing the following (U/L is units per liter and mM is millimoles per liter):

1000 U/L hexokinase
2000 U/L G-6-PDH
2.0 mM ATP
1.0 mM magnesium aspartate
0.25 mM thio-NADP
100000 U/L urease
800 U/L GLDH
10 mM alpha-ketoglutarate
0.25 mM NADH
50 mM TEA pH 8.0

Sample is added to the reagent at a ratio of 1:201 and the reaction is allowed to proceed. The urea is followed at 340 nm by reading every 60 seconds for three minutes. After 3 minutes the absorbance is read at 404 nm. Concentrations are calculated by comparison with standard curves.

EXAMPLE 12

Glucose/Urea Simultaneous Assay

The following procedure describes a method for performing a simultaneous assay for glucose and urea by monitoring the rates of both the glucose and the urea reactions. A reagent system was prepared by mixing the following (U/L is unites per liter and mM is millimoles per liter):

1000 U/L hexokinase
200 U/L G-6-PDH
2.0 mM ATP
1.0 mM magnesium aspartate
0.25 mM thio-NADP
100000 U/L urease
800 U/L GLDH
10 mM alpha ketoglutarate
0.25 mM NADH
50 mM TEA pH 8.0

Sample is added to the reagent at a ratio of 1:201 and the reaction is allowed to proceed. Every 60 seconds for three minutes the absorbance is read at 340 nm and at 404 nm. Concentration are calculated by comparison with standard curves.

EXAMPLE 13

Glucose/Urea Simultaneous Assay

The following procedure describes a method for performing a simultaneous assay for glucose and urea by monitoring the endpoints of both the glucose and the urea reactions. A reagent system was prepared by mixing the following (U/L is units per liter and mM is millimoles per liter):
- 10,000 U/L glucose dehydrogenase
- 2,000 U/L mutarotase
- 0.25 mM thio-NADP
- 25000 U/L GLDH
- 10 mM alpha ketoglutarate
- 0.6 mM NADH
- 50 mM triethanolamine (TEA) pH 8.0

Sample was added to the reagent at a ratio of 1:201 and the reaction was allowed to proceed. After 3 minutes the absorbance was read at 364 nm and at 404 nm. Concentrations were calculated by comparison with standard curves.

EXAMPLE 14

Glucose/Urea Simultaneous Assay

The following procedure describes a method for performing a simultaneous assay for glucose and urea by monitoring the glucose rate of reaction and the urea reaction endpoint. A reagent system was prepared by mixing the following:
- 1000 U/L glucose dehydrogenase
- 200 U/L Mutarotase
- 0.25 mM thio-NADP
- 85000 U/L urease
- 25000 U/L GLDH
- 10 mM alpha ketoglutarate
- 0.6 mM NADH
- 50 mM TEA pH 8.0

Sample was added to the reagent at a ratio of 1:201 and the reaction was allowed to proceed. The glucose rate of reaction was monitored at 404 nm by taking a reading every 60 seconds for three minutes, starting at 60 seconds. After 3 minutes the absorbance is read at 364 nm. Concentrations are calculated by comparison with standard curves.

EXAMPLE 15

Glucose/Urea Simultaneous Assay

The following procedure describes a method for performing a simultaneous assay for glucose and urea by monitoring the glucose reaction endpoint and the urea reaction rate. A reagent system was prepared by mixing the following:
- 10,000 U/L glucose dehydrogenase
- 2,000 U/L Mutarotase
- 0.25 mM thio-NADP
- 50000 U/L urease
- 800 U/L GLDH
- 10 mM alpha ketoglutarate
- 0.6 mM NADH
- 50 mM TEA pH 8.0

Sample was added to the reagent at a ratio of 1:201 and the reaction was allowed to proceed. The urea was followed at 364 nm by reading every 60 seconds for three minutes. After 3 minutes the absorbance is read at 404 nm. Concentrations were calculated by comparison with standard curves.

EXAMPLE 16

Glucose/Urea Simultaneous Assay

The following procedure describes a method for performing a simultaneous assay for glucose and urea by monitoring the glucose reaction rate and the urea reaction rate. A reagent system was prepared by mixing the following:
- 1000 U/L glucose dehydrogenase
- 0.25 mM thio-NADP
- 200 U/L Mutarotase
- 50000 U/L urease
- 800 U/L GLDH
- 10 mM alpha ketoglutarate
- 0.6 mM NADH
- 50 mM Tris pH 8.0

Sample was added to the reagent at a ratio of 1:201 and the reaction was allowed to proceed. Every 60 seconds for three minutes the absorbance is read at 364 nm and at 404 nm. Concentrations were calculated by comparison with standard curves

EXAMPLE 17

Glucose/Urea Simultaneous with Leucine Dehydrogenase

This method would essentially be the same as in Examples 1–8, except the ADH would be replaced with leucine dehydrogenase and the pyruvate would be replaced with 2-oxoisocapnoate (in concentrations suitable for endpoint or rate determination).

EXAMPLE 18

Glucose/Urea Simultaneous with glutamine synthetase

The glucose reaction for this method would be the same as in Examples 5–8. The urea part of the reaction would consist of the following (in concentrations suitable for endpoint or rate determination): urease, glutamine synthetase, ATP, phosphoenolpyruvate, pyruvate kinase, NADH, and LDH.

EXAMPLE 19

Glucose/Urea Simultaneous Assay

The following procedure describes a method for performing a simultaneous assay for glucose and urea which employs a different method than employed in Examples 1–18. The glucose part of the assay consists of hexokinase, G-6-PDH, magnesium, ATP, and NAD(P). The reduction of NAD to NADH is monitored at 340 nm.

The urea part of the assay consists of urease and an indicator dye. The production of ammonia by the action of urease on urea is monitored by a change in color of the indicator dye at 564 nm.

A reagent system was prepared by mixing the following:
- 1000 U/L hexokinase
- 200 U/L G-6-PDH
- 2.0 mM ATP
- 1.0 mM magnesium aspartate
- 0.6 mM NAD
- 100,000 U/L urease
- 0.075 mM Phenol Red
- 50 mM Tartrate (pH 6.8)

The glucose reaction was monitored at 340 nm every 60 seconds for three minutes starting after three minutes. The urea delta absorbance was read at 564 nm after 3 minutes.

EXAMPLE 20

Glucose/Urea Simultaneous Assay

This procedure involves the same urea method as in Example 19. The glucose part of the assay consists of glucose dehydrogenase with NAD(P) as coenzyme for the glucose dehydrogenase. The reduction of NAD to NADH is monitored at 340 nm.

A reagent system was prepared by mixing the following:

50 mM tartrate pH 6.8
0.075 mM Phenol Red
1000 U/L glucose dehydrogenase
200 U/L Mutarotase
0.6 mM NAD
20000 U/L urease The glucose reaction was monitored at 340 nm every 60 seconds for three minutes starting after three minutes. The urea delta absorbance was read at 564 nm after 3 minutes.

EXAMPLE 21

Glucose/Urea Simultaneous Assay

The following procedure describes a method for performing a simultaneous assay for glucose and urea which employs a different method than employed in Examples 1-20. The glucose part of the assay consists of glucose dehydrogenase with DCIP as a coenzyme for the glucose dehydrogenase. The reduction of DCIP is monitored at 600 nm.

The urea part of the assay consists of urease, ADH, pyruvate, oxalate, and NADH as the coenzyme for ADH. The oxidation of NADH to NAD is monitored at 340 nm.

EXAMPLE 22

Glucose/Urea Simultaneous Assay

This procedure uses the same glucose method as in Example 21. The urea part of the assay consists of urease, GLDH, alpha ketoglutarate, and NADH as the coenzyme for GLDH.

EXAMPLE 23

Glucose/Urea Simultaneous Fluorescent Assay

The following procedure describes a method for performing a simultaneous assay for glucose and urea which employs fluorescence to determine the substrate concentration. In this method a spectrofluorometer is used to monitor the simultaneous reactions. The components of the assay are essentially the same as in Example 1. The glucose part of the assay is measured by following the fluorescence emission at 550 with excitation at 400 nm as thio-NADP is reduced to thio-NADPH. The urea part of the assay is measured by following the fluorescence emission at 440 nm with excitation at 340 nm as NADH is oxidized to NAD.

We claim;

1. A method for the simultaneous determination of glucose and urea in a sample with a single reagent system in a reaction mixture comprising:
   adding in a single step a reagent system containing enzymatic reagents and reactants for the simultaneous determination of glucose and urea, each enzymatic reagent and reactant being selected such that it capable of contributing to a discrete electromagnetic radiation signal for either glucose or urea, wherein the determination of glucose does not interfere with the determination of urea, and the determination of urea does not interfere with the determination of glucose;
   simultaneously reacting a sample containing glucose and urea with the reagent system; and
   monitoring changes in absorbance or fluorescence of the resulting reaction mixture at two or more wavelengths, thereby separately but simultaneously determining the concentration of glucose and urea in the sample.

2. A method for the simultaneous determination of glucose and urea in a sample with a single reagent system in a reaction mixture comprising:
   adding in a single step a reagent system containing enzymatic reagents and chromophores for the simultaneous determination of glucose and urea, each enzymatic reagent and chromophore being selected such that it is capable of contributing to a discrete electromagnetic radiation absorbance signal for either glucose or urea, wherein the determination of glucose does not interfere with determination of urea, and the determination of urea does not interfere with the determination of glucose;
   simultaneously reacting sample containing glucose and urea with the reactant system; and
   monitoring changes in absorbance or fluorescence of the resulting reaction mixture at two or more wavelengths, thereby separately but simultaneously determining the concentration of glucose and urea, in the sample.

3. The method of claim 2 wherein said chromophore used in the glucose determination is selected from the group consisting of: NAD(H), NADP(H), thio-NAD(H), thio-NADP(H), hypoxanthine-NAD(H), hypoxanthine-NADP(H), pyrroloquinone and chromogenic oxygen acceptors.

4. The method of claim 2 wherein said chromophore sued in the area determination is selected from the group consisting of: NAD(H), NADP(H), thio-NAD(H), thio-NADP(H), hypoxanthine-NAD(H), hypoxanthine-NADP(H) and pH indicator dyes.

5. The method of claim 2 wherein said reagent comprises an NADP(H)-specific enzyme system for the determination of glucose with thio-NADP(H) as a chromophore; and an NAD(H)-specific enzyme system for the determination of urea with NAD(H) as a chromophore.

6. The method of claim 2 wherein said reagent comprises an NAD(H)-specific enzyme system for the determination of glucose with NAD(H) as a chromophore; and an NAD(H)-specific enzyme system for the determination of urea with thio-NADP(H) as a chromophore.

7. The method of claim 2 wherein said reagent comprises an oxidized or reduced pyrroloquinone-specific enzyme system for the determination of glucose with 2,6-dichlorophenolindophenol as a chromophore; and an NAD(P)(H) enzyme system for the determination of urea with NAD(P)(H) as a chromophore.

8. The method of claim 5 wherein said reagent comprises glucose dehydrogenase and thio-NADP for the determination of glucose; and urease, alpha-ketoglutarate, GLDH, and NADH for the determination of urea.

9. The method of claim 8 which additionally includes mutarotase for the determination of glucose.

10. The method of claim 5 wherein said reagent comprises NADP specific glucose dehydrogenase an thio-NADP for the determination of glucose; and urease, pyruvate, NADH specific ADH, an LDH inhibitor, and NADH for the determination of urea.

11. The method of claim 10 which additionally includes mutarotase for the determination of glucose.

12. The method of claim 5 wherein said reagent comprises NADP specific glucose-6-phosphate dehydrogenase, hexokinase, ATP, Mg and thio-NADP for the determination of glucose; and urease, pyruvate, NADH specific ADH, an LDH inhibitor, and NADH for the determination of urea.

13. The method of claim 5 wherein said reagent comprises NADP specific glucose-6-phosphate dehydrogenase, hexokinase, ATP, Mg and thio-NADP for the determination of glucose; and urease, alpha-ketoglutarate, NADH specific GLDH, and NADH for the determination of urea.

14. The method of claim 5 wherein said reagent comprises NADP specific glucose dehydrogenase and thio-NADP for the determination of glucose; and urease, 2-oxoisocapnoate, NADH specific leucine dehydrogenase, an LDH inhibitor and NADH for the determination of urea.

15. The method of claim 14 which additionally includes mutarotase for the determination of glucose.

16. The method of claim 5 wherein said reagent comprises NADP specific glucose-6-phosphate dehydrogenase, hexokinase, ATP, Mg and thio-NADP for the determination of glucose; and urease, 2-oxoisocapnoate, NADH specific leucine dehydrogenase, an LDH inhibitor and NADH for the determination of urea.

17. The method of claim 5 wherein said reagent comprises NADP specific glucose dehydrogenase and thio-NADP for the determination of glucose; and urease, glutamine synthetase, ATP, phosphoenolpyruvate, pyruvate kinase, NADH specific lactate dehydrogenase, and NADH for the determination of urea.

18. The method of claim 17 which additionally includes mutarotase for the determination of glucose.

19. The method of claim 2 wherein said reagent comprises NAD(P) glucose dehydrogenase and NAD(P) for the determination of glucose; and urease, and a pH indicator dye for the determination of urea.

20. The method of claim 19 which additionally includes mutarotase for the determination of glucose.

21. The method of claim 2 wherein said reagent comprises NAD(P) glucose-6-phosphate dehydrogenase, hexokinase, ATP, Mg and NAD(P) for the determination of glucose; and urease, and a pH indicator dye for the determination of urea.

22. The method of claim 7 wherein said reagent comprises glucose dehydrogenase (E.C.1.1.99.10) and 2,6-dichloroindophenol for the determination of glucose; and urease, alpha-ketoglutarate, GLDH, and NADH for the determination of urea.

23. The method of claim 22 which additionally includes mutarotase for the determination of glucose.

24. The method of claim 7 wherein said reagent comprises glucose dehydrogenase (E.C.1.1.99.10) and 2,6-dichloroindophenol for the determination of glucose; and urease, pyruvate, ADH, an LDH inhibitor, and NAD(P)(H) for the determination of urea.

25. The method of claim 24 which additionally includes mutarotase for the determination of glucose.

26. The method of claim 7 wherein said reagent comprises glucose dehydrogenase (E.C.1.1.99.10) and 2, 6 dichloroindophenol for the determination of glucose; and urease, 2-oxoisocapnoate, leucine dehydrogenase, an LDH inhibitor and NAD(P)(H) for the determination of urea.

27. The method of claim 26 which additionally includes mutarotase for the determination of glucose.

28. The method of claim 7 wherein said reagent comprises glucose dehydrogenase (E.C.1.1.99.10) and 2,6 -dichloroindophenol for the determination of glucose; and urease, glutamine synthetase, ATP, phosphoenolpyruvate, pyruvate kinase, lactate dehydrogenase, NADH for the determination of urea.

29. The method of claim 28 which additionally includes mutarotase for the determination of glucose.

30. The method of claims 1 or 2 wherein the changes in absorbance or fluorescence are monitored by measuring changes in a reaction rate or an endpoint reaction.

31. The method of claim 2 wherein said reagent comprises glucose oxidase, hydrogen peroxide and a chromogenic oxygen acceptor for the determination of glucose; and urease, GLDH, alpha-ketoglutarate and NAD(P)(H) for the determination of urea.

32. The method of claim 2 wherein said reagent comprises glucose oxidase, hydrogen peroxide and a chromogenic oxygen acceptor for the determination of glucose; and urease, ADH, pyruvate, an LDH inhibitor and NAD(P)(H) for the determination of urea.

33. The method of claim 2 wherein said reagent comprises glucose oxidase, hydrogen peroxide and a chromogenic oxygen acceptor for the determination of glucose; and urease, leucine dehydrogenase, 2-oxoisocaproate, an LDH inhibitor and NAD(P)(H) for the determination of urea.

34. The method of claim 2 wherein said reagent comprises glucose oxidase, hydrogen peroxide and a chromogenic oxygen acceptor for the determination of glucose; and urease, glutamine synthetase, ATP, phosphoenol-pyruvate, pyruvate kinase, lactate dehydrogenase and NAD(P)(H) for the determination of urea.

* * * * *